US009481856B2

(12) United States Patent
Xia et al.

(10) Patent No.: US 9,481,856 B2
(45) Date of Patent: Nov. 1, 2016

(54) PHARMACEUTICAL FORMULATIONS COMPRISING STABILIZED POLYSACCHARIDES AND SOURCE OF HYDROGEN PEROXIDE

(75) Inventors: Erning Xia, Penfield, NY (US); Michael E. Allen, Webster, NY (US); Steven K. MacLeod, Henrietta, NY (US); Tammy J. Kleiber, Rochester, NY (US); Craig M. Cody, Scottsville, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1992 days.

(21) Appl. No.: 12/468,136

(22) Filed: May 19, 2009

(65) Prior Publication Data

US 2009/0304811 A1 Dec. 10, 2009

Related U.S. Application Data

(60) Provisional application No. 61/059,940, filed on Jun. 9, 2008.

(51) Int. Cl.

| *A61K 33/40* | (2006.01) |
| *C11D 3/00* | (2006.01) |
| *A61K 9/00* | (2006.01) |
| *A61K 9/08* | (2006.01) |
| *A61K 31/715* | (2006.01) |
| *A61K 31/726* | (2006.01) |
| *A61K 31/728* | (2006.01) |
| *A61K 31/734* | (2006.01) |
| *A61K 47/08* | (2006.01) |
| *A61K 47/10* | (2006.01) |
| *A61K 47/36* | (2006.01) |
| *A61L 12/12* | (2006.01) |
| *A61L 12/14* | (2006.01) |
| *C11D 3/22* | (2006.01) |
| *C11D 3/39* | (2006.01) |

(52) U.S. Cl.
CPC ........... *C11D 3/0078* (2013.01); *A61K 9/0048* (2013.01); *A61K 9/08* (2013.01); *A61K 31/715* (2013.01); *A61K 31/726* (2013.01); *A61K 31/728* (2013.01); *A61K 31/734* (2013.01); *A61K 33/40* (2013.01); *A61K 47/08* (2013.01); *A61K 47/10* (2013.01); *A61K 47/36* (2013.01); *A61L 12/124* (2013.01); *A61L 12/14* (2013.01); *A61L 12/145* (2013.01); *C11D 3/222* (2013.01); *C11D 3/3947* (2013.01)

(58) Field of Classification Search
CPC .................................................. A61K 31/734
See application file for complete search history.

(56) References Cited

U.S. PATENT DOCUMENTS

| 5,576,028 | A | 11/1996 | Martin et al. |
| 5,607,698 | A | 3/1997 | Martin et al. |
| 5,660,862 | A | 8/1997 | Park et al. |
| 5,725,887 | A | 3/1998 | Martin et al. |
| 5,776,445 | A | 7/1998 | Cohen et al. |
| 5,807,585 | A | 9/1998 | Martin et al. |
| 6,528,465 | B1 | 3/2003 | Cantoro |
| 7,485,619 | B2 * | 2/2009 | Kim et al. ............... 514/1.1 |
| 2003/0232089 | A1 | 12/2003 | Singh et al. |
| 2006/0057105 | A1 * | 3/2006 | Stern et al. ............. 424/85.4 |
| 2006/0127497 | A1 | 6/2006 | Karagoezian |
| 2007/0207116 | A1 | 9/2007 | Brown |

FOREIGN PATENT DOCUMENTS

| EP | 0354186 B1 | 8/1996 |
| EP | 1464341 A1 | 10/2004 |
| EP | 1759702 A1 | 3/2007 |
| GB | 2173017 A | 10/1986 |
| WO | WO 2008/074853 A1 | 6/2008 |
| WO | WO 2009/111170 A1 | 9/2009 |

OTHER PUBLICATIONS

Labbe et al., "Comparison of toxicological profiles of benzalkonium chloride and polyquaternium-1: an experimental study," J of Ocular Pharm & Thera, 2006, (vol. 22), (Issue. 4), (p. 267-279).
Haug et al., "A study of the constitution of alginic acid by partial acid hydrolysis," Acta Chemica Scand, 1966, (vol. 20), (p. 183-190).
Klock et al., "Biocompatibility of mannuronic acid-rich alginates," Biomaterials, 1997, (vol. 18), (p. 707-713).
Martindale, "The Complete Drug Reference," Nonionic Surfactants, 34th ed., (p. 1411-1416).
Remington, "The Science and Practice of Pharmacy," Nonionic Agents, 21st ed., (p. 291).
Swarbrick et al., "Part 2: Pharmaceutics," Chapter 22: Coarse Dispersions, (p. 319-337).

* cited by examiner

*Primary Examiner* — Zohreh Fay
(74) *Attorney, Agent, or Firm* — Toan P. Vo

(57) ABSTRACT

A pharmaceutical formulation that is effective in adversely affecting the viability of microorganisms or in inhibiting their growth and that provides better safety and/or comfort to the users comprises a polysaccharide, a source of hydrogen peroxide, and an anti-oxidant. The formulation can further comprise a chelating agent and/or an ophthalmically active agent for treating or controlling a disease or disorder of the eye. The formulation may be used to treat, clean, disinfect, store, wet, or rewet contact lenses.

7 Claims, No Drawings

PHARMACEUTICAL FORMULATIONS COMPRISING STABILIZED POLYSACCHARIDES AND SOURCE OF HYDROGEN PEROXIDE

CROSS-REFERENCE

This application claims the benefit of Provisional Patent Application No. 61/059,940 filed Jun. 9, 2008, which is incorporated by reference herein.

BACKGROUND

The present invention relates to pharmaceutical formulations comprising stabilized polysaccharides and a source of hydrogen peroxide. In particular, the present invention relates to such formulations that are used in ophthalmic applications and provide improved safety and/or comfort to the users.

Pharmaceutical formulations are commonly provided in multi-use bottles. Formulations, such as ophthalmic compositions, find uses in many ophthalmic applications. These compositions are often instilled directly into the eye one or more times a day to either deliver medications or to relieve symptoms of eye conditions, such as dry eye or inflammation of the superficial tissues of the eye accompanying various allergic reactions (such as hay fever allergies and the like, irritation of the eye due to foreign bodies, or eye fatigue). Other ophthalmic solutions are employed in the field of contact-lens care. Contact-lens solutions are utilized to soak, disinfect, clean, and wet contact lenses. These solutions are not instilled directly in the eye from the bottle, but do subsequently come into contact with the eye when the lenses are placed on the eye.

Ophthalmic compositions are provided sterile, but once opened, are susceptible to microbial contamination. In the case of multi-use solutions, the formulations contain at least a preservative designed to kill microorganisms that come in contact with the solution, protecting the patient from infection due to a contaminated ophthalmic solution during the prescribed usage.

Typically, preservatives for ophthalmic compositions fall into two traditional categories: alcohols and amines or ammonium-containing compounds. Typical alcohol-based anti-microbial agents include benzyl alcohol, phenethyl alcohol, and chlorbutanol. Alcohol-based preservatives work by disorganizing the lipid structure of cell membrane, and thus increase permeability of the cell wall, leading to cell lysis. These alcohols have limited solubility in aqueous solutions and tend not to be stable preservatives due to being susceptible to oxidation, evaporation, and interaction with the plastic bottle. More commonly, organic amines and ammonium-containing compounds are utilized as anti-microbial agents in ophthalmic solutions. Representative compounds in this category include benzalkonium chloride ("BAK"), benzododecinium bromide ("BDD"), chlorhexidine, polymeric biguanide (such as polyhexamethylene biguanide or "PHMB"). It is believed that the electrophilicity of the nitrogen-containing moieties of these compounds promotes their interaction with the negatively charged cell membranes of the microorganisms, leading to cell lysis, and thus severely impacting their survival.

Although amines and ammonium-containing compounds have good anti-microbial activity, and are used commercially to preserve ophthalmic solutions, there are significant disadvantages associated with these compounds. In particular, these compounds used at higher doses can be toxic to the sensitive tissues of the eye. For example, BAK-containing ophthalmic solutions are known to cause eye irritation in patients. It causes growth arrest at very low concentration (0.00001%), apoptosis at 0.01%, and necrosis at higher concentrations (0.05-0.1%). Patients who may be at greater risk of BAK-induced adverse effects are those with dry-eye syndrome since they often need to use eye drop over an extended period of time. Polymeric amines and ammonium-containing compounds are less toxic than BAK but still can cause irritation responses in some other patients. For example, polyquaternium-1 ($\alpha$-4-{tris(2hydroxyethyl)ammonium-2-butenyl} poly {1-dimethylammonium-2-butenyl}-$\omega$-tris(2-hydroxyethyl)ammonium chloride), also known as Polyquad®, has been shown to be less toxic than BAK and used in a limited number of ophthalmic formulations. However, polyquaternium-1 still shows some adverse effects on ocular tissues. A 0.5% polyquaternium-1 formulation has been shown significantly to decrease goblet cell density. Healthy goblet cells are required to produce adequate mucin, which is one of three component layers of the tear film. A. Labbé et al., *J. Ocular Pharmacol. & Therapeutics*, Vol. 22, No. 4, 267 (2006). Chlorhexidine, on the other hand, has proven to be more biocompatible than the other amines and ammonium-containing anti-microbial agents and, therefore, non-irritating at the levels typically used. However, the mildness of chlorhexidine to the ocular environment is offset by the fact that chlorhexidine is a relatively weak preservative.

Oxidative preservatives, which work by oxidizing cell walls or membranes, affecting membrane-bound enzymes, and disrupting cellular function. U.S. Pat. Nos. 5,576,028; 5,607,698; 5,725,887; and 5,807,585 and European Patent 035486 disclose solutions, which may be ophthalmic solutions or contact lens solutions, containing from 10 ppm (0.001%) to 1000 ppm (0.1%) hydrogen peroxide and a hydrogen peroxide stabilizer. However, the long-term preservative efficacy of these solutions is not known. It is suggested in these patents that hydrogen peroxide concentration should be in trace amounts in order to be tolerable to the patient upon direct application. At trace concentrations, stabilizers are needed to prevent decomposition of hydrogen peroxide.

On the other hand, various polysaccharides have been used as viscosity modifiers or drug delivery agents in pharmaceutical compositions. For example, the use of alginate as a thickener for topical ophthalmic use is disclosed in U.S. Pat. No. 6,528,465 and U.S. Patent Application Publication 2003/0232089. U.S. Pat. No. 5,776,445 discloses the use of alginate as a drug delivery agent that is topically applied to the eye. U.S. Patent Application Publication 2003/0232089 teaches a dry-eye formulation that contains two polymer ingredients including alginate.

However, polysaccharides are not normally compatible with oxidative agents in pharmaceutical compositions. Thus, the preparation of useful compositions comprising polysaccharides and oxidative preservatives presents a significant technical challenge to people in the field.

Therefore, there is a continued need to provide improved pharmaceutical formulations that comprise a polysaccharide and an effective preservative that provides improved safety and/or comfort to the users. It is also very desirable to provide improved ophthalmic solutions having such advantages.

SUMMARY

In general, the present invention provides improved pharmaceutical formulations that comprise a polysaccharide and an effective preservative.

In one aspect, such formulations provide improved safety and/or comfort to the users.

In another aspect, such a preservative is effective in adversely affecting the viability of microorganisms or in inhibiting their growth and provides better safety and/or comfort to the users.

In still another aspect, a pharmaceutical formulation of the present invention comprises at least a polysaccharide, at least a source of hydrogen peroxide, and at least an anti-oxidant.

In yet another aspect, a pharmaceutical formulation of the present invention comprises at least a polysaccharide, at least a source of hydrogen peroxide, at least an anti-oxidant, and at least a stabilizer for said source of hydrogen peroxide.

In a further aspect, such a pharmaceutical formulation is an ophthalmic solution, which provides less irritation to ocular tissues and more lubricity to ocular surfaces than prior-art solutions.

In still another aspect, said polysaccharide comprises alginic acid or a pharmaceutically acceptable salt thereof.

In yet another aspect, said at least a source of hydrogen peroxide is present in an effective amount to inhibit or prevent the survival of microorganisms.

In still another aspect, representatives of such microorganisms comprise *Staphylococcus aureus, Pseudomonas aeruginosa, Eschrechia coli, Candida albicans*, and *Aspergillus niger*.

In a further aspect, said stabilizer for said source of hydrogen peroxide comprises a chelating agent.

In still another aspect, a formulation of the present invention further comprises boric acid.

In yet another aspect, a pharmaceutical formulation of the present invention is free of a material selected from the group consisting of cationic organic nitrogen-containing preservatives, alcoholic preservatives, and mixtures thereof.

In a further aspect, the present invention provides a method for making a pharmaceutical formulation. The method comprises combining at least a polysaccharide, at least a source of hydrogen peroxide, and at least an anti-oxidant to form the pharmaceutical formulation.

In still another aspect, the present invention provides a method for providing safety, or comfort, or both to users of a pharmaceutical formulation. The method comprises adding at least a polysaccharide, at least a source of hydrogen peroxide, and at least an anti-oxidant to the pharmaceutical formulation.

In yet another aspect, the present invention provides a method for treating, controlling, or preventing a condition of an eye that manifests irritation or inflammation. The method comprises topically administering to the eye an effective amount of an ophthalmic solution that comprises at least a polysaccharide, at least a source of hydrogen peroxide, and at least an anti-oxidant to relieve such irritation or inflammation.

In a further aspect, the present invention provides a method for treating an ophthalmic device. The method comprises contacting the ophthalmic device with an ophthalmic solution comprising at least a polysaccharide, at least a source of hydrogen peroxide, and at least an anti-oxidant.

In still a further aspect, the ophthalmic device is a contact lens.

Other features and advantages of the present invention will become apparent from the following detailed description and claims.

DETAILED DESCRIPTION

In general, the present invention provides improved pharmaceutical formulations that provide improved safety and/or comfort to the users.

In one aspect, the present invention provides an ophthalmic composition that provides comfort to a user and is effective in adversely affecting the viability of microorganisms or in inhibiting their growth therein, methods of making, and methods of using such formulations. Within the scope of the present invention, the microorganisms that are adversely affected by a formulation of the present invention include microorganisms selected from the group consisting of bacteria, yeasts, molds, and mixtures thereof.

In one aspect, pharmaceutical formulations of the present invention can kill or adversely affect the survival or propagation of such microorganisms. In one embodiment, representatives of such microorganisms comprise *Staphylococcus aureus* (or *S. aureus*), *Pseudomonas aeruginosa* (or *P. aeruginosa*), *Eschrechia coli* (or *E. coli*), *Candida albicans* (or *C. albicans*), and *Aspergillus niger* (or *A. niger*).

In another aspect, a pharmaceutical formulation of the present invention comprises at least a polysaccharide, at least a source of hydrogen peroxide.

As used herein, the term "polysaccharide" includes branched or unbranched polymeric carbohydrate chains, wherein the main chain comprises three or more sugar units (or alternatively called "residues") linked together. In one embodiment, the main chain comprises from 3 to about 100000 sugar units. In some other embodiments, the main chain comprises from 3 to about 75000 sugar units (or alternatively, from 10 to about 50000, or from 50 to about 100000, or from 50 to about 50000, or from 50 to about 25000, or from 50 to about 10000, or from 50 to about 5000, or from 100 to about 100000, or from 100 to about 50000, or from 100 to about 25000, or from 100 to about 10000, or from 100 to about 5000 sugar units). Each sugar unit may independently comprise three, four, five, or six carbon atoms.

In still another aspect, the polysaccharide is selected from the group consisting of alginic acid, gellan gum, β-glucan, guar gum, gum arabic (a mixture of arabinogalactan oligosaccharides, polysaccharides, and glycoproteins), locust bean gum, pectin, xanthan gum, hyaluronic acid, carboxymethyl starch, carboxymethyl dextran, dextran sulfate, carboxymethyl chitosan, chondroitin sulfate (e.g., chondroitin sulfate A, chondroitin sulfate B, or chondroitin sulfate C), carrageenan, curdlan gum, carboxymethyl cellulose, methyl cellulose, hydroxypropyl cellulose, hydroxypropyl methyl cellulose, hydroxyethyl methyl cellulose, pharmaceutically acceptable salts thereof, derivatives thereof, and mixtures thereof. It should be understood that some of the polysaccharides enumerated above may not have naturally occurring salts.

In some embodiments, the polysaccharide is selected from the group consisting of alginic acid, carboxymethyl cellulose, carboxymethyl starch, carboxymethyl dextran, hyaluronic acid, pharmaceutically acceptable salts thereof, derivatives thereof, combinations thereof, and mixtures thereof. In other embodiments, the polysaccharide is selected from the group consisting of pharmaceutically acceptable salts of alginic acid, carboxymethyl cellulose, carboxymethyl starch, carboxymethyl dextran, hyaluronic acid; derivatives thereof, combinations thereof; and mixtures thereof. In still another embodiment, the polysaccharide is selected from the group consisting of physiologically acceptable salts of alginic acid, carboxymethyl starch, carboxymethyl dextran; derivatives thereof, combinations thereof, and mixtures thereof. In still another embodiment, the polysaccharide is selected from the group consisting of pharmaceutically acceptable salts of alginic acid, carboxymethyl starch, carboxymethyl dextran, carboxymethyl chitosan, chondroitin sulfate; derivatives thereof, combinations thereof, and mixtures thereof.

In yet another aspect, the polysaccharide comprises alginic acid or a pharmaceutically acceptable salt thereof.

Alginate, for the purpose of this application is a polysaccharide that comprises monomeric units of β-D-mannuronic acid and α-L-guluronic acid, or salts thereof, or derivatives of such acids or salts.

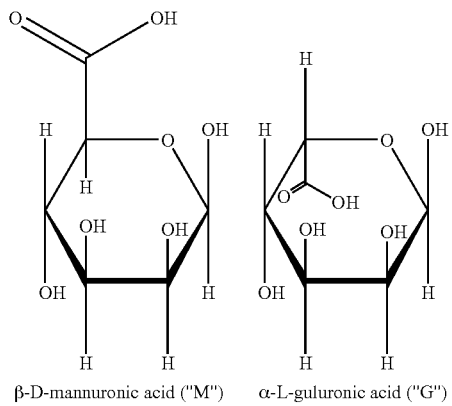

β-D-mannuronic acid ("M")    α-L-guluronic acid ("G")

Some alginate polymers are block copolymers with blocks of the guluronic acid (or a salt thereof) monomeric units alternating with blocks of the mannuronic acid (or a salt thereof) monomeric units. Other alginate molecules have alternating single monomeric units of guluronic acid (or a salt thereof) and mannuronic acid (or a salt thereof). The ratio and distribution of the M and G components along with the average molecular weight affect the physical and chemical properties of the copolymer. See A. Haug et al., *Acta Chem Scand*, Vol. 20, 183-190 (1966). Alginate polymers have viscoelastic rheological properties and other properties that make it suitable for some medical applications. See G. Klock et al., "Biocompatibility of Mannuronic Acid-Rich Alginates," *Biomaterials*, Vol. 18, No. 10, 707-713 (1997).

In certain embodiments, said alginate has a molecular weight in a range from about 50 kDa to about 5000 kDa. Alternatively, said alginate has a molecular weight in a range from about 50 kDa to about 2000 kDa (or from about 50 kDa to about 1000 kDa, or from about 50 kDa to about 700 kDa, from about 50 kDa to about 500 kDa, or from about 50 kDa to about 100 kDa, or from about 100 kDa to about 2000 kDa, or from about 100 kDa to about 1000 kDa, or from about 100 kDa to about 500 kDa, or from about 500 kDa to about 2000 kDa, or from about 500 kDa to about 1000 kDa). Suitable alginates are known under the trade name Protanal, available from FMC BioPolymer, Philadelphia, Pa.

In one preferred embodiment, the molecular weight is about 200-300 kDa.

The proportion of G monomeric units in an alginate molecule suitable for a composition of the present invention can be in the range from about 10 to about 90 percent of the total number of monomeric units of the alginate molecule. Alternatively, such proportion can be in the range from about 20 to about 75 (or from 30 to about 60, or from about 25 to about 50, or from about 20 to about 50, or from about 10 to about 30) percent of the total number of monomeric units of the alginate molecule. In one embodiment, such proportion is about 35-45 percent.

In a further aspect, polysaccharide comprises hyaluronic acid or a pharmaceutically acceptable salt thereof.

In one embodiment, the pharmaceutical formulation comprises an ophthalmic solution.

In still another aspect, an ophthalmic solution of the present invention provides less irritation to ocular tissues and more lubricity to ocular surfaces than prior-art solutions.

In yet another aspect, said at least a source of hydrogen peroxide is present in an effective amount to inhibit or prevent the survival of microorganisms. In one embodiment, the effectiveness of the solution is determined according to a testing procedure disclosed below.

In one embodiment, said at least a source of hydrogen peroxide comprises a compound or material that release hydrogen peroxide into the formulation. In another embodiment, such a compound or material is selected from the group consisting of hydrogen peroxide, urea hydrogen peroxide (carbamide peroxide, carbamide perhydrate, or percarbamide), perborate salts, derivatives thereof, combinations thereof, and mixtures thereof.

In another embodiment, said at least a source of hydrogen peroxide is present in an amount effective to adversely affect the viability of microorganisms or inhibit their growth. In still another embodiment, said amount is effective to reduce the concentration of viable bacteria, recovered per milliliter of the formulation, at the fourteenth day after challenge, by not less than 3 logs, and after a rechallenge at the fourteenth day, said amount is also effective to reduce the concentration of viable bacteria, recovered per milliliter of the formulation, at the twenty-eighth day, by not less than 3 logs. In addition, said amount is effective to keep the concentration of viable yeasts and molds, recovered per milliliter of the formulation, at or below the initial concentration (within an experimental uncertainty of ±0.5 log) at the fourteenth day, and after a rechallenge at the fourteenth day, said amount is also effective to keep the concentration of viable yeasts and molds, recovered per milliliter of the formulation, at or below the initial concentration (within an experimental uncertainty of ±0.5 log) at the twenty-eighth day.

In still another embodiment, the amount of hydrogen peroxide generated in a pharmaceutical formulation of the present invention is in the range from about 0.0001 to about 5 percent by weight of the formulation. Alternatively, the amount of hydrogen peroxide is in the range from about 0.001 to about 3 percent, or from about 0.001 to about 1 percent, or from greater than about 0.01 to about 2 percent, or from greater than about 0.01 to about 1 percent, or from greater than about 0.01 to about 0.7 percent, or from greater than about 0.01 to about 0.5 percent, or from greater than about 0.01 to about 0.2 percent, or from greater than about 0.01 to about 0.1 percent, or from greater than about 0.01 to about 0.07 percent, or from greater than about 0.01 to about 0.05 percent, or from greater than about 0.05 to about 0.15 percent, or from greater than about 0.03 to about 0.15 percent by weight of the solution, or from greater than about 0.1 to about 1 percent, or from greater than about 0.1 to about 0.7 percent, or from greater than about 0.1 to about 0.5 percent, or from greater than about 0.1 to about 0.2 percent, or from greater than about 0.1 to about 0.15 percent. Preferably, the amount of hydrogen peroxide in a formulation of the present invention throughout its shelf life is greater than about 0.01% by weight of the total formulation.

In another aspect, the polysaccharide comprises an anionic derivative of a polysaccharide.

The present inventors surprisingly discovered that the presence of a polysaccharide in a formulation comprising hydrogen peroxide or a source thereof can provide ocular comfort to a user, which comfort is typically not experienced by the user with compositions having hydrogen peroxide or a source thereof in which such a polysaccharide is absent, especially at a relative high concentration of hydrogen peroxide. The present inventors surprisingly further discovered that such a formulation can be prepared to form a stable composition that include said polysaccharide, said hydrogen peroxide or source thereof, and an anti-oxidant. In one aspect, a "stable composition" means a composition wherein the polysaccharide does not degrade to an extent that results in a decrease in the viscosity of the composition of more than 50 percent upon storage at about 25° C. for a period of 1 month.

In one embodiment, the amount of the polysaccharide in an ophthalmic solution of the present invention is in the range from about 0.01 to about 10 percent by weight of the solution. Alternatively, the amount of the polysaccharide is in the range from about 0.01 to about 5 percent, or from about 0.02 to about 2 percent, or from about 0.05 to about 1 percent, or from about 0.1 to about 0.5 percent by weight of the solution. In another embodiment, the polysaccharide is present in the solution in an amount sufficient to provide lubrication to an ocular surface, such as the corneal or the conjunctiva.

In yet another aspect, an ophthalmic solution of the present invention is free of a material selected from the group consisting of cationic organic nitrogen-containing compounds, such as cationic organic nitrogen-containing small molecules or polymers; alcohols; and mixtures thereof.

An ophthalmic solution of the present invention can further comprise one or more other ingredients, such as therapeutic agents that target specific eye conditions, buffers, tonicity adjusting agents, surfactants, viscosity adjusting agents, chelating agents, anti-oxidants, or other components.

In some embodiments, a composition of the present invention advantageously comprises a polysaccharide, an anti-oxidant, and a chelating agent.

Non-limiting examples of anti-oxidants include ascorbic acid (vitamin C) and its salts and esters; tocopherols (such as α-tocopherol) and tocotrienols (vitamin E), and their salts and esters (such as vitamin E TGPS (D-α-tocopheryl polyethylene glycol 1000 succinate)); glutathione; lipoic acid; uric acid; butylated hydroxyanisole ("BHA"); butylated hydroxytoluene ("BHT"); tertiary butylhydroquinone ("TBHQ"); and polyphenolic anti-oxidants (such as gallic acid, cinnanmic acid, flavonoids, and their salts, esters, and derivatives). In some embodiments, the anti-oxidant comprises ascorbic acid (vitamin C) and its salts and esters; tocopherols (such as α-tocopherol) and tocotrienols (vitamin E), and their salts and esters; or BHA.

In still another embodiment, the amount of an anti-oxidant in a pharmaceutical formulation of the present invention is in the range from about 0.0001 to about 5 percent by weight of the formulation. Alternatively, the amount of an anti-oxidant is in the range from about 0.001 to about 3 percent, or from about 0.001 to about 1 percent, or from greater than about 0.01 to about 2 percent, or from greater than about 0.01 to about 1 percent, or from greater than about 0.01 to about 0.7 percent, or from greater than about 0.01 to about 0.5 percent, or from greater than about 0.01 to about 0.2 percent, or from greater than about 0.01 to about 0.1 percent, or from greater than about 0.01 to about 0.07 percent, or from greater than about 0.01 to about 0.05 percent, or from greater than about 0.05 to about 0.15 percent, or from greater than about 0.03 to about 0.15 percent by weight of the solution, or from greater than about 0.1 to about 1 percent, or from greater than about 0.1 to about 0.7 percent, or from greater than about 0.1 to about 0.5 percent, or from greater than about 0.1 to about 0.2 percent, or from greater than about 0.1 to about 0.15 percent.

Non-limiting chelating agents include compounds having Formula I, II, or III.

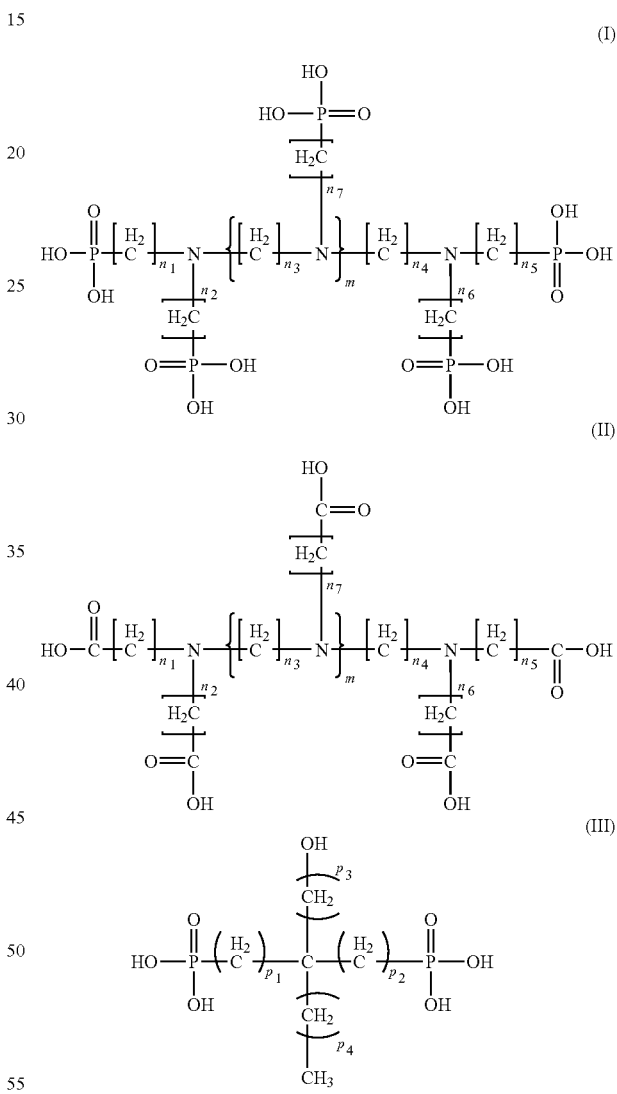

wherein $n_1$, $n_2$, $n_3$, $n_4$, $n_5$, $n_6$, and $n_7$ are integers independently in the range from 1 to 4, inclusive; m is an integer in the range from 1 to 3, inclusive; $p_1$, $p_2$, $p_3$, and $p_4$ are independently selected from 0 and integers in the range from 1 to 4, inclusive.

In some embodiments, the chelating agent comprises a compound selected from the group consisting of ethylenediaminetetraacetic acid ("EDTA"), diethylenetriaminepentakis(methylphosphonic acid), etidronic acid, pharmaceutically acceptable salts thereof, and mixtures thereof.

In some other embodiments, the chelating agent comprises tetrasodium salt of etidronic acid (also known as "HAP", which is available as 30% solution).

In still some other embodiments, the chelating agent comprise EDTA sodium salt.

Furthermore, an ophthalmic solution of the present invention can comprise a therapeutic agent such as anti-inflammatory agents, antibiotics, immunosuppressive agents, antiviral agents, antifungal agents, antiprotozoal agents, combinations thereof, or mixtures thereof. Non-limiting examples of anti-inflammatory agents include glucocorticosteroids (e.g., for short-term treatment) and non-steroidal anti-inflammatory drugs ("NSAIDs").

Non-limiting examples of the glucocorticosteroids are: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, their physiologically acceptable salts, derivatives thereof, combinations thereof, and mixtures thereof. In one embodiment, the therapeutic agent is selected from the group consisting of difluprednate, loteprednol etabonate, prednisolone, combinations thereof, and mixtures thereof.

Non-limiting examples of the NSAIDs are: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cimnetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, S-(5'-adenosyl)-L-methionine, 3-amino-4-hydroxybutyric acid, amixetrine, bendazac, benzydamine, α-bisabolol, bucolome, difenpiramide, ditazol, emorfazone, fepradinol, guaiazalene, nabumetone, nimesulide, oxaceprol, paranyline, perisoxal, proquazone, superoxide dismutase, tenidap, zileuton, their physiologically acceptable salts, combinations thereof, and mixtures thereof.

Non-limiting examples of antibiotics include doxorubicin; aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin SV, rifapentine, rifaximin), β-lactams (e.g., carbacephems (e.g., loracarbet)), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforamide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefininox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin S, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Other examples of antibiotics are the synthetic antibacterials, such as 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-B, chloramine-T, dichloramine T, $n^2$-formylsulfisomidine, $n^4$-β-D-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene citrate, methenamine hippurate, methenamine mandelate, methenamine sulfosalicylate, nitroxoline, taurolidine, xibomol).

Non-limiting examples of immunosuppressive agents include dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefir, enocitabine, floxuridine, fluorouracil, gemcitabine, tegafur), fluocinolone, triaminolone, anecortave acetate, fluorometholone, medrysone, and prednisolone.

Non-limiting examples of antifungal agents include polyenes (e.g., amphotericin B, candicidin, dermostatin, filipin, fungichromin, hachimycin, hamycin, lucensomycin, mepartricin, natamycin, nystatin, pecilocin, perimycin), azaserine, griseofulvin, oligomycins, neomycin undecylenate, pyiroInitrin, siccanin, tubercidin, viridin, allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole), acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

Non-limiting examples of antiviral agents include acyclovir, carbovir, famciclovir, ganciclovir, penciclovir, and zidovudine.

Non-limiting examples of antiprotozoal agents include pentamidine isethionate, quinine, chloroquine, and mefloquine.

An ophthalmic solution of the present invention can be formulated in a physiologically acceptable buffer to regulate pH and tonicity in a range compatible with ophthalmic uses and with any active ingredients present therein. Non-limiting examples of physiologically acceptable buffers include phosphate buffer; a Tris-HCl buffer (comprising tris(hydroxymethyl)aminomethane and HCl); buffers based on HEPES (N-{2-hydroxyethyl}peperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; TES (N-tris{hydroxymethyl}-methyl-2-aminoethanesulfonic acid) having $pK_a$ of 7.4 at 25° C. and pH in the range of about 6.8-8.2; MOBS (4-{N-morpholino}butanesulfonic acid) having $pK_a$ of 7.6 at 25° C. and pH in the range of about 6.9-8.3; DIPSO (3-(N,N-bis{2-hydroxyethyl}amino)-2-hydroxypropane)) having $pK_a$ of 7.52 at 25° C. and pH in the range of about 7-8.2; TAPSO (2-hydroxy-3 {tris(hydroxymethyl)methylamino}-1-propanesulfonic acid)) having $pK_a$ of 7.61 at 25° C. and pH in the range of about 7-8.2; TAPS ({(2-hydroxy-1,1-bis(hydroxymethyl)ethyl)amino}-1-propanesulfonic acid)) having $pK_a$ of 8.4 at 25° C. and pH in the range of about 7.7-9.1; TABS (N-tris(hydroxymethyl)methyl-4-aminobutanesulfonic acid) having $pK_a$ of 8.9 at 25° C. and pH in the range of about 8.2-9.6; AMPSO(N-(1,1-dimethyl-2-hydroxyethyl)-3-amino-2-hydroxypropanesulfonic acid)) having $pK_a$ of 9.0 at 25° C. and pH in the range of about 8.3-9.7; CHES (2-cyclohexylamino)ethanesulfonic acid) having $pK_a$ of 9.5 at 25° C. and pH in the range of about 8.6-10.0; CAPSO (3-(cyclohexylamino)-2-hydroxy-1-propanesulfonic acid) having $pK_a$ of 9.6 at 25° C. and pH in the range of about 8.9-10.3; or CAPS (3-(cyclohexylamino)-1-propane sulfonic acid) having $pK_a$ of 10.4 at 25° C. and pH in the range of about 9.7-11.1.

While the buffer itself is a "tonicity adjusting agent" and a "pH adjusting agent" that broadly maintains the ophthalmic solution at a particular ion concentration and pH, additional "tonicity adjusting agents" can be added to adjust the final tonicity of the solution. Such tonicity adjusting agents are well known to those of skill in the art and include, but are not limited to, mannitol, sorbitol, dextrose, sucrose, urea, propylene glycol, and glycerin. Also, various salts, including halide salts of a monovalent cation (e.g., NaCl or KCl) can be utilized.

The tonicity adjusting agent, when present, can be in a concentration ranging from about 0.01 to about 10, or from about 0.01 to about 7, or from about 0.01 to about 5, or from about 0.1 to about 2, or from about 0.1 to about 1 percent by weight. In some embodiments where a tonicity adjusting agent is present the solution can contain a single agent or a combination of different tonicity adjusting agents. Typically, the tonicity of a formulation of the present invention is in the range from about 200 to 400 mOsm/kg. Alternatively, the tonicity of a formulation of the present invention is in the range from about 220 to 400 mOsm/kg, or from about 220 to 350 mOsm/kg, or from about 220 to 300 mOsm/kg, or from about 250 to 350 mOsm/kg, or from about 250 to 300 mOsm/kg, or from about 240 to 280 mOsm/kg. For relief of dry eye symptoms, an ophthalmic formulation of the present invention may be desirably hypotonic, such as having tonicity in the range from about 200 to about 270 mOsm/kg.

Ophthalmic solutions of the present invention also can comprise one or more surfactants. Suitable surfactants can include cationic, anionic, non-ionic or amphoteric surfactants. Preferred surfactants are neutral or nonionic surfactants. Non-limiting examples of surfactants suitable for a formulation of the present invention include polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® 127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, $34^{th}$ ed., pp 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., pp 291 and the contents of chapter 22, Lippincott Williams & Wilkins, New York, 2006. The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1 weight percent).

In some embodiments, the ophthalmic solutions of this invention can optionally include other viscosity adjusting agents (e.g., particularly when the ophthalmic solution is intended to act as a lubricant (i.e., artificial tear)). Suitable viscosity adjusting agents for administration to an eye are well known to those of skill in the art. One or more polysaccharides disclosed above can act as viscosity adjusting agents. Other non-ionic polysaccharides such as cellulose derivatives are commonly used to increase viscosity, and as such, can offer other advantages. Specific cellulose derivatives include, but are not limited to hydroxypropyl methyl cellulose, carboxymethyl cellulose, methyl cellulose, or hydroxyethyl cellulose. Typically, particularly when used as an artificial tear, the ophthalmic solution has a viscosity from about 1 to about 1000 centipoises (or mPa·s). As a solution, the present pharmaceutical formulation is usually dispensed in the eye in the form of an eye drop. It should be understood, however, that the present pharmaceutical formulation may also be formulated as a viscous liquid (e.g., viscosities from 50 to several thousand cps), gel, or ointment, which has even higher viscosity, for ophthalmic or non-ophthalmic uses. Furthermore, in some contact-lens related embodiments, lenses may be soaked or otherwise exposed to a pharmaceutical formulation of the present invention prior to wear.

In some embodiments, an ophthalmic formulation of the present invention can further comprise a demulcent. Polysaccharides, such as those disclosed herein above can act as demulcents. Other demulcents also can be included, such as those approved by the U.S. Food and Drug Administration ("US FDA") and listed in 21 C.F.R. Part 349. They include hypromellose (0.2 to 2.5 percent), dextran 70 (0.1 percent when used with another polymeric demulcent listed in this regulation), gelatin (0.01 percent), liquid polyols, glycerin (0.2 to 1 percent), polyethylene glycol 300 or 400 (0.2 to 1 percent), propylene glycol (0.2 to 1 percent), polyvinyl alcohol (0.1 to 4 percent), povidone (or polyvinyl pyrrolidone, 0.1 to 2 percent). All compositions are in percent by weight of the total formulation, unless otherwise indicated.

In some other embodiments, a pharmaceutical formulation may include one or more emollients, such as those listed in 21 C.F.R. Section 349.14.

In addition to those classes of ingredients disclosed above, a pharmaceutical formulation, such as an ophthalmic solution, of the present invention can further comprise one or more other ingredients, such as vitamins (other than those disclose hereinabove), or other ingredients that provide added health benefits to the users. Where an ophthalmic solution is intended for contact-lens care, it can comprise other known components that are generally used for cleaning and maintenance of contact lenses, as long as these components are compatible with other ingredients in the formulation. In one embodiment, a contact-lens care solution can comprise microabrasives (e.g., polymer microbeads).

In another embodiment, a pharmaceutical formulation of the present invention can further comprise a second preservative. In some embodiments, said second preservative is polyquatemium-1. In still some embodiments, said second preservative is other than a material selected from the group consisting of cationic organic nitrogen-containing compounds and alcohols. In still some other embodiments, said second preservative is present in an amount such that the concentration of the source of hydrogen peroxide provides hydrogen peroxide at a concentration less than about 0.1%, or less than about 0.03%, or less than about 0.01% by weight of the total formulation. In still some other embodiments, said second preservative is polyquaternium-1 and is present in an amount such that the concentration of the source of hydrogen peroxide provides hydrogen peroxide at a concentration less than about 0.1%, or less than about 0.03%, or less than about 0.01% by weight of the total formulation. In still another embodiment, said second preservative comprises another oxidative preservative, such as stabilized oxychloro complex (an equilibrium mixture of oxychloro species). In still another embodiment, such a stabilized oxychloro complex is present in an amount from about 0.001 to about 0.01% by weight of the total formulation.

In another aspect, the present invention provides a method for preparing a pharmaceutical formulation that comprises at least a polysaccharide, at least a source of hydrogen peroxide, and at least an anti-oxidant. The method comprises adding said at least a polysaccharide, at least a source of hydrogen peroxide, and at least an anti-oxidant to a formulation.

In still another aspect, the method further comprises adding at least a chelating agent to said formulation. In some embodiments, the chelating agents comprises a compound disclosed above.

Formulation Compounding Procedure

In one aspect, a pharmaceutical formulation of the present invention can be prepared by a method comprising the step of: (a) adding a predetermined amount of a source of hydrogen peroxide into a vessel containing 80-90 percent of a desired volume of purified water; (b) adding predetermined amounts of other desired ingredients, such as therapeutic, nutritional, or prophylactic ingredients, which target a desired physiological condition, into the vessel; (c) adding a desired amount of at least a chelating agent to the vessel to form a first mixture; (d) adding a predetermined amount of at least a polysaccharide to the first mixture to form a second mixture; (e) adding purified water to the vessel to bring the total volume of the second mixture to 100 percent of the desired volume; and (f) mixing the contents of the vessels to produce the pharmaceutical formulation. The method can further comprise subjecting the pharmaceutical formulation to sterilization by heating, autoclaving and/or filtration through a desired filter. Optionally, the method also can comprise adding one or more additional ingredients to the second mixture, which additional ingredients are selected from the group consisting of buffers, tonicity adjusting agents, surfactants, demulcents, emollients, viscosity adjusting agents, other vitamins, other ingredients that provide added health benefits to the users, and mixtures thereof.

Procedure for Evaluating the Preservative Efficacy ("PE") of a Pharmaceutical Formulation of the Present Invention Against Microorganisms The microorganisms against which the PE of a pharmaceutical formulation of the present invention is evaluated are *S. aureus*, *E. coli*, *P. aeruginosa*, *C. albicans*, and *A. niger*. This procedure applies to the US FDA premarket notification (510(k)) guidance document and ISO/DIS 14730 standard preservative efficacy testing with a 14-day rechallenge. The evaluations were conducted with 3 separate lots of each test solution for each microorganism. Each lot was tested with a different preparation of each microorganism.

Bacterial cells were grown on Tryptic Soy Agar ("TSA") slants at a temperature in the range from 30 to 35° C. in an incubator for a time period from 18 to 24 hours. Fungal cells were grown on Sabouraud Dextrose Agar ("SDA") slants at a temperature in the range from 20° C. to 25° C. in an incubator for a time period of 2 to 7 days. Cells were harvested in saline solution (5-10 ml, USP, 0.9% saline, with or without 0.1% Tween 80 surfactant, which was added to each agar slant, followed by gentle agitation with a sterile cotton swab. The cell suspensions were aseptically dispensed into separate sterile polypropylene centrifuge tubes. Cells were harvested by centrifugation at 3000 rpm for 10 minutes, washed one time, and suspended in Saline TS to a concentration of $2 \times 10^8$ cells per ml.

The cell suspension (0.1 ml) was diluted with 20 ml of the test solution to reach a final concentration of from $1.0 \times 10^5$ to $1.0 \times 10^6$ colony-forming units ("CFU"). Phosphate Buffered Saline ("PBS") was used as a control solution. The inoculated test and control solutions were incubated at a temperature ranging from 20° C. to 25° C. in static culture. At time zero, 1 ml of PBS (USP, pH 7.2) from the control solution was diluted with 9 ml of PBS and serially diluted cells were plated in triplicate on TSA for bacteria and SDA for fungi. The bacterial plates were incubated at a temperature ranging from 30 to 35° C. for a period ranging from 2 to 4 days. Fungal plates were incubated at a temperature ranging from 20 to 25° C. for a period ranging from 2 to 7 days.

Similarly, at days 7 and 14, a one-milliliter volume from a test solution was added into 9 ml of Dey-Engley neutralizing broth ("DEB") and serially diluted in DEB and plated in triplicate on TSA for bacteria and SDA for fungi. The bacterial plates were incubated at a temperature ranging from 30 to 35° C. for a period ranging from 2 to 4 days. Fungal plates were incubated at a temperature ranging from 20° C. to 25° C. for a period ranging from 2 to 7 days. Developing colonies were counted.

Immediately following the day 14 sampling, test solutions were re-inoculated to give final concentrations of from $1.0 \times 10^4$ to $1.0 \times 10^5$ of each microorganism. At time zero, 1 ml from the inoculum control was added to 9 ml of PBS and subsequent serial dilutions were plated in triplicate on TSA for bacteria and SDA for fungi. The bacterial plates were incubated at a temperature ranging from 30 to 35° C. for a period ranging from 2 to 4 days. Fungal plates were incubated at a temperature ranging from 20 to 25° C. for a period ranging from 2 to 7 days.

At days 21 and 28, 1 ml from the test articles was added to 9 ml of DEB and again, serial dilutions were plated in triplicate on TSA. Plates were incubated at a temperature ranging from 30 to 35° C. for a period ranging from 2 days to 4 days and developing colonies counted.

Based on the acceptance criteria for bacteria, a solution is acceptable if the concentration of viable bacteria, recovered per milliliter, is reduced by at least 3 logs at day 14, and after a rechallenge at day 14, the concentration of bacteria is reduced by at least 3 logs by day 28. In addition, the solution is acceptable if the concentration of viable yeasts and molds, recovered per milliliter of the solution, remains at or below the initial concentration (within an experimental uncertainty of ±0.5 log) at day 14, and after a rechallenge at day 14, the concentration of viable yeasts and molds remains at or below the initial concentration (within an experimental uncertainty of ±0.5 log) at day 28.

The results at the fourteenth and twenty-eighth days for the tested solutions are shown in the following section as log reduction in the concentration of the applicable microorganism.

Example 1

First Series of Formulations

The first series of formulations had the following compositions.

| Ingredient | % w/w (except pH, Osmolality, and Viscosity) | | | |
|---|---|---|---|---|
| | 1 | 2 | 3 | 4 |
| Boric acid | 0.55 | 0.55 | 0.55 | 0.55 |
| Sodium borate | 0.035 | 0.035 | 0.035 | 0.035 |
| Alginate (Protanal LF200M) | 0.25 | 0.25 | 0.25 | 0.25 |
| Glycerin | 0.6 | 0.6 | 0.6 | 0.6 |
| Propylene glycol | 0.6 | 0.6 | 0.6 | 0.6 |
| Urea hydrogen peroxide | 0.162 | 0.162 | 0.162 | 0.162 |
| EDTA | 0.05 | absent | 0.05 | 0.05 |
| BHA | absent | absent | absent | 0.05 |
| pH at initial time | 6.55 | 6.85 | 6.85 | 6.44 |
| pH after one month in storage at 25° C. | 6.11 | 5.59 | 6.86 | 6.19 |
| pH after three months in storage at 25° C. | 4.92 | 4.21 | 6.80 | 6.35 |
| Osmolality (mOsm/kg) at initial time | 287 | 282 | 284 | 290 |
| Osmolality (mOsm/kg) after one month in storage at 25° C. | 280 | 281 | 289 | 285 |

-continued

|   | % w/w (except pH, Osmolality, and Viscosity) | | | |
| --- | --- | --- | --- | --- |
| Ingredient | 1 | 2 | 3 | 4 |
| Osmolality (mOsm/kg) after three months in storage at 25° C. | 280 | 279 | 281 | 289 |
| Viscosity (mPa · s) at initial time | 8.6 | 3.9 | 10 | 9.8 |
| Viscosity (mPa · s) after one month in storage at 25° C. | 3.8 | 1.1 | 5.5 | 8.7 |
| Viscosity (mPa · s) after three months in storage at 25° C. | 1.8 | 1.1 | 2.3 | 6.1 |
| Preservative Efficacy ("PE") | passed | passed | passed | passed |

PE Test Result—after 4 weeks in storage at 25° C.

|   | Days after | Formulation | | | |
| --- | --- | --- | --- | --- | --- |
| Organism | Challenge | 1 | 2 | 3 | 4 |
| S. aureus | 14 days | >4.9 | >4.9 | >4.9 | >4.9 |
|   | 28 days | >4.9 | >4.9 | >4.9 | >4.9 |
| P. aeruginosa | 14 days | >4.8 | >4.8 | >4.8 | >4.8 |
|   | 28 days | >4.8 | >4.8 | >4.8 | >4.8 |
| E. coli | 14 days | >4.7 | >4.7 | >4.7 | >4.7 |
|   | 28 days | >4.7 | >4.7 | >4.7 | >4.7 |
| C. albicans | 14 days | >4.9 | >4.9 | >4.9 | >4.9 |
|   | 28 days | >4.9 | >4.9 | >4.9 | >4.9 |
| A. niger | 14 days | 2.6 | 3.2 | 4.3 | 1.7 |
|   | 28 days | 2.8 | 4.5 | >4.5 | 2.1 |

PE Test Result—after 4 weeks in storage at 40° C.

|   | Days after | Formulation | | | |
| --- | --- | --- | --- | --- | --- |
| Organism | Challenge | 1 | 2 | 3 | 4 |
| S. aureus | 14 days | >4.9 | >4.9 | >4.9 | >4.9 |
|   | 28 days | >4.9 | >4.9 | >4.9 | >4.9 |
| P. aeruginosa | 14 days | >4.8 | >4.8 | >4.8 | >4.8 |
|   | 28 days | >4.8 | >4.8 | >4.8 | >4.8 |
| E. coli | 14 days | >4.7 | >4.7 | >4.7 | >4.7 |
|   | 28 days | >4.7 | >4.7 | >4.7 | >4.7 |
| C. albicans | 14 days | >4.9 | >4.9 | >4.9 | >4.9 |
|   | 28 days | >4.9 | >4.9 | >4.9 | >4.9 |
| A. niger | 14 days | 2.2 | 2.6 | 3.0 | 2.3 |
|   | 28 days | 3.7 | 4.3 | 4.3 | 3.0 |

Example 2

Second Series of Formulations

The second series of formulations had the following compositions.

|   | % w/w (except pH, Osmolality, and Viscosity) | | | |
| --- | --- | --- | --- | --- |
| Ingredient | 5 | 6 | 7 | 8 |
| Boric acid | 0.55 | 0.55 | absent | absent |
| Sodium borate | 0.035 | 0.035 | absent | absent |
| Alginate (Protanal LF200M) | 0.25 | 0.25 | 0.25 | 0.25 |
| Sodium phosphate monobasic | absent | absent | 0.08 | 0.08 |
| Sodium phosphate dibasic | absent | absent | 0.089 | 0.089 |
| Glycerin | 0.6 | 0.6 | 0.6 | 0.6 |
| Propylene glycol | 0.6 | 0.6 | 0.6 | 0.6 |
| Urea hydrogen peroxide | 0.162 | 0.162 | 0.162 | 0.162 |
| HAP (30%) | 0.1 | 0.1 | 0.1 | 0.1 |
| BHA | absent | 0.01 | absent | 0.01 |
| pH at initial time | 7.11 | 7.15 | 7.15 | 7.14 |
| pH after one month in storage at 25° C. | 7.03 | 7.1 | 7.11 | 7.18 |
| pH after two months in storage at 25° C. | 6.74 | 7.1 | 7 | 7.18 |
| Osmolality (mOsm/kg) at initial time | 285 | 285 | 219 | 218 |
| Osmolality (mOsm/kg) after one month in storage at 25° C. | 286 | 288 | 221 | 221 |
| Osmolality (mOsm/kg) after two months in storage at 25° C. | 285 | 287 | 218 | 221 |
| Viscosity (mPa · s) at initial time | 9.3 | 9.3 | 7.3 | 7.2 |
| Viscosity (mPa · s) after one month in storage at 25° C. | 3.1 | 8.3 | 2.8 | 6 |
| Viscosity (mPa · s) after two months in storage at 25° C. | 1.9 | 7.9 | 2 | 5.1 |
| Preservative Efficacy ("PE") | passed | passed | passed | passed |

PE Test Result at 25° C.—first challenge on day of formulation preparation

|   | Days after | Formulation | | | |
| --- | --- | --- | --- | --- | --- |
| Organism | Challenge | 5 | 6 | 7 | 8 |
| S. aureus | 14 days | >4.9 | >4.9 | >4.9 | >4.9 |
|   | 28 days | >4.9 | >4.9 | >4.9 | >4.9 |
| P. aeruginosa | 14 days | >4.8 | >4.8 | >4.8 | >4.8 |
|   | 28 days | >4.8 | >4.8 | >4.8 | >4.8 |
| E. coli | 14 days | 4.9 | >4.9 | >4.9 | >4.7 |
|   | 28 days | >4.9 | >4.9 | >4.9 | >4.7 |
| C. albicans | 14 days | >4.9 | >4.9 | >4.9 | >4.9 |
|   | 28 days | >4.9 | >4.9 | >4.9 | >4.9 |
| A. niger | 14 days | 2.5 | 0.9 | 4.3 | 1.7 |
|   | 28 days | 2.8 | 1.3 | >4.5 | 2.1 |

Example 3

Third Series of Formulations

The third series of formulations had the following compositions.

|   | % w/w (except pH, Osmolality, and Viscosity) | | | | |
| --- | --- | --- | --- | --- | --- |
| Ingredient | 9 | 10 | 11 | 12 | 13 |
| Boric acid | 0.5 | 0.5 | 0.5 | 0.5 | 0.5 |
| Sodium borate | 0.014 | 0.014 | 0.014 | 0.014 | 0.014 |
| Alginate (Protanal LF200M) | 0.25 | 0.25 | 0.25 | 0.25 | 0.25 |

| Ingredient | % w/w (except pH, Osmolality, and Viscosity) | | | | |
|---|---|---|---|---|---|
| | 9 | 10 | 11 | 12 | 13 |
| Glycerin | 0.6 | 0.6 | 0.6 | 0.6 | 0.6 |
| Propylene glycol | 0.6 | 0.6 | 0.6 | 0.6 | 0.6 |
| Urea hydrogen peroxide | 0.162 | absent | absent | absent | absent |
| Sodium perborate $H_2O$ | absent | 0.05 | 0.1 | absent | absent |
| Sodium perborate $4H_2O$ | absent | absent | absent | 0.05 | 0.1 |
| HAP (30%) | 0.1 | 0.1 | 0.1 | 0.1 | 0.1 |
| pH at initial time | 7.01 | 7.56 | 7.76 | 7.56 | 7.84 |
| pH after one month in storage at 25° C. | 6.94 | 7.51 | 7.72 | 7.49 | 7.72 |
| pH after two months in storage at 25° C. | 6.77 | 7.44 | 7.66 | 7.40 | 7.64 |
| Osmolality (mOsm/kg) at initial time | 276 | 248 | 257 | 248 | 257 |
| Osmolality (mOsm/kg) after one month in storage at 25° C. | 269 | 248 | 254 | 247 | 254 |
| Osmolality (mOsm/kg) after two months in storage at 25° C. | 270 | 248 | 254 | 247 | 255 |
| Viscosity (mPa · s) at initial time | 9.7 | 8.4 | 7.7 | 8.5 | 7.6 |
| Viscosity (mPa · s) after one month in storage at 25° C. | 4.5 | 5.8 | 4.5 | 4.8 | 3.3 |
| Viscosity (mPa · s) after two months in storage at 25° C. | 2.2 | 4.0 | 3.0 | 2.9 | 2.1 |
| Preservative Efficacy ("PE") | passed | passed | Passed | passed | passed |

PE Test Result at 25° C.—first challenge on day of formulation preparation

| Organism | Days after Challenge | 9 | 10 | 11 | 12 | 13 |
|---|---|---|---|---|---|---|
| S. aureus | 14 days | >4.7 | >4.7 | >4.7 | >4.7 | >4.7 |
| | 28 days | >4.7 | >4.7 | >4.7 | >4.7 | >4.7 |
| P. aeruginosa | 14 days | >4.7 | >4.7 | >4.7 | >4.7 | >4.7 |
| | 28 days | >4.7 | >4.7 | >4.7 | >4.7 | >4.7 |
| E. coli | 14 days | >4.6 | >4.6 | >4.6 | >4.6 | >4.6 |
| | 28 days | >4.6 | >4.6 | >4.6 | >4.6 | >4.6 |
| C. albicans | 14 days | >4.6 | >4.6 | >4.6 | >4.6 | >4.6 |
| | 28 days | >4.6 | >4.6 | >4.6 | >4.6 | >4.6 |
| A. niger | 14 days | >4.6 | 2.0 | 2.1 | 0.9 | 4.3 |
| | 28 days | >4.6 | 1.8 | 3.2 | 1.9 | >4.6 |

Example 4

Fourth Series of Formulations

The fourth series of formulations had the following compositions.

| Ingredient | % w/w (except pH, Osmolality, and Viscosity) | | | | | |
|---|---|---|---|---|---|---|
| | 14 | 15 | 16 | 17 | 18 | 19 |
| Boric acid | 0.5 | 0.5 | 0.5 | 0.5 | 0.5 | 0.5 |
| Sodium borate | 0.014 | 0.014 | 0.014 | 0.014 | 0.014 | 0.014 |
| Alginate (Protanal LF200M) | 0.25 | 0.25 | 0.25 | 0.25 | 0.25 | 0.25 |
| Glycerin | 0.6 | 0.6 | 0.6 | 0.6 | 0.6 | 0.6 |
| Propylene glycol | 0.6 | 0.6 | 0.6 | 0.6 | 0.6 | 0.6 |
| Urea hydrogen peroxide | 0.162 | absent | absent | 0.162 | absent | absent |
| Sodium perborate $4H_2O$ | absent | 0.1 | 0.2 | absent | 0.1 | 0.2 |
| HAP (30%) | 0.05 | 0.05 | 0.05 | 0.05 | 0.05 | 0.05 |
| BHA | absent | absent | absent | 0.01 | 0.01 | 0.01 |
| pH at initial time | 6.85 | 7.61 | 7.84 | 6.85 | 7.61 | 7.86 |
| pH after one month in storage at 25° C. | 6.85 | 7.58 | 7.83 | 6.82 | 7.59 | 7.81 |
| pH after two months in storage at 25° C. | 6.80 | 7.55 | 7.78 | 6.86 | 7.53 | 7.77 |
| Osmolality (mOsm/kg) at initial time | 272 | 249 | 257 | 272 | 250 | 259 |
| Osmolality (mOsm/kg) after one month in storage at 25° C. | 274 | 250 | 259 | 275 | 254 | 279 |
| Osmolality (mOsm/kg) after two months in storage at 25° C. | 272 | 249 | 260 | 277 | 257 | 279 |
| Viscosity (mPa · s) at initial time | 10.8 | 8.4 | 7.5 | 11 | 8.4 | 7.4 |

-continued

| Ingredient | 14 | 15 | 16 | 17 | 18 | 19 |
|---|---|---|---|---|---|---|
| | % w/w (except pH, Osmolality, and Viscosity) | | | | | |
| Viscosity (mPa · s) after one month in storage at 25° C. | 6.6 | 5.8 | 3.9 | 9.9 | 7.7 | 6.1 |
| Viscosity (mPa · s) after two months in storage at 25° C. | 4.7 | 3.8 | 2.5 | 4.0 | 7.5 | 4.5 |
| Preservative Efficacy ("PE") | passed | passed | passed | passed | passed | passed |

In some embodiments, one or more pharmaceutical active ingredients suitable for ophthalmic administration are included in a pharmaceutical formulation of the present invention for treatment or control of an ophthalmic disorder or disease. Non-limiting examples of such formulations are shown below.

Example 5

Ophthalmic Formulation With Anti-Inflammatory Drug

The following ingredients are combined to produce such a formulation.

| Ingredient | % w/w |
|---|---|
| Sodium Borate | 0.02 |
| Boric Acid | 0.5 |
| Glycerin | 0.6 |
| Propylene Glycol | 0.6 |
| Sodium Alginate (Protanal LF200M) | 0.25 |
| Urea Hydrogen Peroxide | 0.1 |
| HAP (30%) | 0.05 |
| BHA | 0.01 |
| Diclofenac Sodium | 0.5 |

Example 6

Ophthalmic Formulation for Treating or Controlling High Intraocular Pressure

The following ingredients are combined to produce an exemplary formulation for treating or controlling high intraocular pressure.

| Ingredient | % w/w |
|---|---|
| Sodium Borate | 0.05 |
| Boric Acid | 0.6 |
| Glycerin | 0.75 |
| Propylene Glycol | 0.3 |
| Sodium Alginate (Protanal LF200M) | 0.3 |
| Urea Hydrogen Peroxide | 0.07 |
| HAP (30%) | 0.1 |
| BHA | 0.01 |
| Timolol Maleate | 0.5 |
| Dorzolamide hydrochloride | 2 |

Example 7

Ophthalmic Formulation for Treating or Controlling Eye Infection

The following ingredients are combined to produce such a formulation.

| Ingredient | % w/w |
|---|---|
| Sodium Borate | 0.02 |
| Boric Acid | 0.5 |
| Glycerin | 0.6 |
| Propylene Glycol | 0.6 |
| Sodium Alginate (Protanal LF200M) | 0.25 |
| Urea Hydrogen Peroxide | 0.1 |
| EDTA | 0.05 |
| BHA | 0.05 |
| Moxifloxacin | 0.5 |

Example 8

Ophthalmic Formulation for Treating or Controlling Eye Infection

The following ingredients are combined to produce such a formulation.

| Ingredient | % w/w |
|---|---|
| Sodium Borate | 0.02 |
| Boric Acid | 0.5 |
| Glycerin | 1 |
| Propylene Glycol | 0.2 |
| Sodium Alginate (Protanal LF200M) | 0.25 |
| Urea Hydrogen Peroxide | 0.1 |
| HAP (30%) | 0.05 |
| vitamin E TGPS | 0.05 |
| Gatifloxacin | 0.3 |
| Ciprofloxacin | 0.15 |

Example 9

Ophthalmic Formulation for Treating or Controlling Eye Infection

The following ingredients are combined to produce such a formulation.

| Ingredient | % w/w |
| --- | --- |
| Sodium Borate | 0.03 |
| Boric Acid | 0.35 |
| Glycerin | 0.6 |
| Propylene Glycol | 0.6 |
| Sodium Alginate (Protanal LF200M) | 0.25 |
| EDTA | 0.05 |
| Urea Hydrogen Peroxide | 0.1 |
| Ascorbic acid | 0.05 |
| 7-[(3R)-3-aminohexahydro-1H-azepin-1-yl]-8-chloro-1-cyclopropyl-6-fluoro-1,4-dihydro-4-oxo-3-quinolinecarboxylic acid monohydrochloride | 0.3 |

Example 10

Ophthalmic Formulation for Treating or Controlling Eye Allergy

The following ingredients are combined to produce an exemplary formulation for treating or controlling eye allergy.

| Ingredient | % w/w |
| --- | --- |
| Sodium Borate | 0.06 |
| Boric Acid | 0.7 |
| Glycerin | 0.6 |
| Propylene Glycol | 0.6 |
| Sodium Alginate (Protanal LF200M) | 0.25 |
| Urea Hydrogen Peroxide | 0.1 |
| Diethylenetriaminepentakis (methylphosphonic acid) sodium salt | 0.05 |
| Gallic acid | 0.05 |
| Ketotifen Fumarate | 0.025 |

Example 11

Ophthalmic Formulation for Treating or Controlling Eye Allergy

The following ingredients are combined to produce an exemplary formulation for treating or controlling eye allergy.

| Ingredient | % w/w |
| --- | --- |
| Sodium Borate | 0.06 |
| Boric Acid | 0.7 |
| Glycerin | 0.6 |
| Propylene Glycol | 0.6 |
| Sodium Alginate (Protanal LF200M) | 0.25 |
| Sodium perborate 4H$_2$O | 0.07 |
| Cinnamic acid | 0.05 |
| EDTA disodium | 0.05 |
| HAP (30%) | 0.02 |
| Olopatadine Hydrochloride | 0.1 |

Example 12

Ophthalmic Formulation for Treating or Controlling Eye Infection

The following ingredients are combined to produce an exemplary formulation for treating or controlling eye infection.

| Ingredient | % w/w |
| --- | --- |
| Sodium Borate | 0.06 |
| Boric Acid | 0.7 |
| Glycerin | 0.6 |
| Propylene Glycol | 0.6 |
| Sodium Alginate (Protanal LF200M) | 0.25 |
| Sodium perborate monohydrate | 0.1 |
| Sodium perborate tetrahydrate | 0.05 |
| Vitamin E TPGS | 0.1 |
| HAP (30%) | 0.1 |
| Acyclovir | 0.05 |

Example 13

Ophthalmic Formulation for Treating or Controlling Eye Infection

The following ingredients are combined to produce an exemplary formulation for treating or controlling eye infection. The polysaccharide included in this formulation is carboxymethyl cellulose.

| Ingredient | % w/w |
| --- | --- |
| Sodium Borate | 0.06 |
| Boric Acid | 0.7 |
| Glycerin | 0.6 |
| Propylene Glycol | 0.6 |
| Carboxymethyl cellulose | 0.25 |
| Urea Hydrogen Peroxide | 0.1 |
| Ascorbic acid | 0.1 |
| HAP (30%) | 0.1 |
| BHA | 0.02 |
| 7-[(3R)-3-aminohexahydro-1H-azepin-1-yl]-8-chloro-1-cyclopropyl-6-fluoro-1,4-dihydro-4-oxo-3-quinolinecarboxylic acid monohydrochloride | 0.3 |

Example 14

Ophthalmic Formulation for Treating or Controlling Eye Inflammation

The following ingredients are combined to produce an exemplary formulation for treating or controlling eye inflammation.

| Ingredient | % w/w |
| --- | --- |
| Sodium Borate | 0.06 |
| Boric Acid | 0.7 |
| Glycerin | 0.6 |
| Propylene Glycol | 0.6 |
| Sodium hyaluronate | 0.25 |
| Urea Hydrogen Peroxide | 0.1 |
| Resveratrol | 0.075 |
| Ascorbic acid | 0.025 |

| Ingredient | % w/w |
| --- | --- |
| HAP (30%) | 0.1 |
| Loteprednol Etabonate | 0.5 |

Example 15

Ophthalmic Formulation for Treating or Controlling Eye Inflammation

The following ingredients are combined to produce an exemplary formulation for treating or controlling eye inflammation.

| Ingredient | % w/w |
| --- | --- |
| Sodium Borate | 0.06 |
| Boric Acid | 0.7 |
| Glycerin | 0.6 |
| Propylene Glycol | 0.6 |
| Chondroitin sulfate | 0.25 |
| Sodium perborate tetrahydrate | 0.1 |
| Diethylenetriaminepentakis(methylphosphonic acid) sodium salt | 0.05 |
| BHA | 0.05 |
| Loteprednol Etabonate | 0.5 |
| Tobramycin | 0.3 |

Example 16

Ophthalmic Formulation for Treating or Controlling Eye Inflammation

The following ingredients are combined to produce an exemplary formulation for treating or controlling eye inflammation.

| Ingredient | % w/w |
| --- | --- |
| Sodium Borate | 0.06 |
| Boric Acid | 0.7 |
| Mannitol | 0.6 |
| Propylene Glycol | 0.6 |
| Carboxymethyl dextran | 0.25 |
| Urea Hydrogen Peroxide | 0.1 |
| Vitamin E TPGS | 0.05 |
| HAP (30%) | 0.05 |
| Dexamethasone | 0.1 |

Example 17

Ophthalmic Formulation for Treating or Controlling Intraocular Pressure

The following ingredients are combined to produce an exemplary formulation for treating or controlling intraocular pressure.

| Ingredient | % w/w |
| --- | --- |
| Sodium Borate | 0.06 |
| Boric Acid | 0.7 |
| Sorbitol | 0.6 |
| Propylene Glycol | 0.6 |
| Sodium Alginate | 0.25 |
| Urea Hydrogen Peroxide | 0.1 |
| Vitamin E TPGS | 0.1 |
| BHA | 0.075 |
| Brimonidine tartrate | 2 |
| Timolol maleate | 0.5 |

Example 18

Formulation Comprising a Second Preservative

The following ingredients are combined to produce an exemplary formulation. This formulation may be used as a vehicle for an ophthalmic active agent or as a contact-lens treating, cleaning, wetting, or storing solution.

| Ingredient | % w/w |
| --- | --- |
| Sodium Borate | 0.06 |
| Boric Acid | 0.7 |
| Glycerin | 0.6 |
| Propylene Glycol | 0.6 |
| Sodium Alginate | 0.25 |
| Sodium perborate monohydrate | 0.03 |
| BHT | 0.05 |
| Gallic acid | 0.05 |
| Polyquaternium-1 | 0.05 |

Example 19

Formulation Comprising a Second Preservative

The following ingredients are combined to produce an exemplary formulation. This formulation may be used as a vehicle for an ophthalmic active agent or as a contact-lens treating, cleaning, wetting, or storing solution.

| Ingredient | % w/w |
| --- | --- |
| Sodium Borate | 0.06 |
| Boric Acid | 0.7 |
| Propylene Glycol | 1 |
| Sodium Alginate | 0.4 |
| Urea Hydrogen Peroxide | 0.05 |
| EDTA disodium | 0.02 |
| HAP (30%) | 0.05 |
| Anthocyanin (anti-oxidant) | 0.06 |
| Stabilized Oxychloro Complex | 0.01 |

In another aspect, an ophthalmic solution of the present invention comprising a polysaccharide, a source of hydrogen peroxide, boric acid, and at least a suitable ophthalmic active ingredient can be used to treat ocular conditions such as dry eye, inflammation, allergy, or infection of the eye.

In still another aspect, the present invention provides methods of making and using a pharmaceutical formulation of the present invention. Any of the materials, compounds, and ingredients disclosed herein is applicable for use with or inclusion in any method of the present invention.

In still another aspect, the present invention provides a method for making a pharmaceutical formulation. The method comprises providing at least a polysaccharide, at least a source of hydrogen peroxide, at least an anti-oxidant, and at least a chelating agent in the pharmaceutical formulation. In one embodiment, the method comprises: (a) providing an initial formulation; and (b) adding said at least a polysaccharide, said at least a source of hydrogen peroxide, said at least an anti-oxidant, and said at least a chelating agent to the initial formulation to produce the pharmaceutical formulation. In another embodiment, the method further comprises adding another ingredient selected from the group consisting of therapeutic agents, buffers, tonicity adjusting agents, surfactants, viscosity adjusting agents, and other agents to the pharmaceutical formulation. The therapeutic agents can be selected from the group of anti-inflammatory agents, agents for lowering intraocular pressure, ocular neuroprotectants, antibiotics, immunosuppressive agents, anti-allergic agents, antiviral agents, antifungal agents, antiprotozoal agents, and mixtures thereof. In still another embodiment, the source of hydrogen peroxide comprises a compound that is soluble in an aqueous medium. Non-limiting examples of each of these classes of agents, compounds, and ingredients are disclosed throughout the present specification.

In still another aspect, the present invention provides a method for making a pharmaceutical formulation. The method comprises providing at least a polysaccharide, boric acid, a source of hydrogen peroxide in the pharmaceutical formulation, a chelating agent, and an anti-oxidant. In one embodiment, the method comprises: (a) providing an initial formulation comprising boric acid, said at least a source of hydrogen peroxide, and said chelating agent; and (b) adding said at least a polysaccharide and said anti-oxidant to the initial formulation to produce the pharmaceutical formulation. The method can further comprise adding an ophthalmically active agent to the pharmaceutical formulation. In one embodiment, said ophthalmically active agent is capable of providing treatment or control of an ophthalmic condition or disorder.

In still another aspect, the present invention provides a method for providing safety, or comfort, or both to users of a pharmaceutical formulation. The method comprises adding a polysaccharide, a source of hydrogen peroxide, a chelating agent, and an anti-oxidant to the pharmaceutical formulation. In one embodiment, the source of hydrogen peroxide is a compound that generates hydrogen peroxide in an aqueous medium. In another embodiment, the polysaccharide is selected from the group consisting of alginic acid, gellan gum, β-glucan, guar gum, gum arabic (a mixture of arabinogalactan ologosaccharides, polysaccharides, and glycoproteins), locust bean gum, pectin, xanthan gum, hyaluronic acid, carboxymethyl starch, carboxymethyl dextran, dextran sulfate, carboxymethyl chitosan, chondroitin sulfate (e.g., chondroitin sulfate A, chondroitin sulfate B, or chondroitin sulfate C), carrageenan, curdlan gum, carboxymethyl cellulose, methyl cellulose, hydroxypropyl cellulose, hydroxypropyl methyl cellulose, hydroxyethyl methyl cellulose, pharmaceutically acceptable salts thereof, derivatives thereof, and mixtures thereof. In another embodiment, the polysaccharide is selected from the group consisting of alginic acid, carboxymethyl cellulose, carboxymethyl starch, carboxymethyl dextran, hyaluronic acid, physiologically acceptable salts thereof, derivatives thereof, combinations thereof, and mixtures thereof. In still another embodiment, the polysaccharide is selected from the group consisting of physiologically acceptable salts of alginic acid, carboxymethyl cellulose, carboxymethyl starch, carboxymethyl dextran, hyaluronic acid; derivatives thereof; combinations thereof; and mixtures thereof.

In yet another aspect, the present invention provides a method for treating, controlling, or preventing a condition of an eye that manifests dryness (for lack of adequate tear production) or requires rewetting, allergy, irritation, or inflammation. The method comprises topically administering to the eye an effective amount of an ophthalmic solution that comprises a polysaccharide, a source of hydrogen peroxide, a chelating agent, and an anti-oxidant to relieve such dryness, allergy, irritation, or inflammation. In one embodiment, the method is used for treating a dry eye condition. In another embodiment, the method for treating or relieving symptoms of dry eye comprises administering to an ocular surface an effective amount of an ophthalmic solution that comprises a polyanionic material, a source of hydrogen peroxide, a demulcent, a tonicity adjusting agent, and a buffering agent. The concentration of each of polysaccharide, source of hydrogen peroxide, chelating agent, and anti-oxidant is selected from among the ranges disclosed herein.

In a further aspect, the present invention provides a method for treating an ophthalmic device. The method comprises contacting the ophthalmic device with an ophthalmic solution comprising a polysaccharide, a source of hydrogen peroxide, and an anti-oxidant. In some embodiments, the solution further comprises a chelating agent. In some other embodiments, the ophthalmic solution has the capability to clean, disinfect, and wet or rewet the ophthalmic device. In still some other embodiments, the ophthalmic solution further comprises an amount of boric acid and/or a pharmaceutically acceptable salt thereof. In yet other embodiments, the ophthalmic solution comprises a polysaccharide, a source of hydrogen peroxide, a chelating agent, an anti-oxidant, a surfactant, and a tonicity adjusting agent. The ophthalmic solution can further comprise a buffering agent.

In still a further aspect, the ophthalmic device is a contact lens.

In a further aspect, the present invention provides a use of a polysaccharide, a source of hydrogen peroxide, and an anti-oxidant for the preparation of a pharmaceutical formulation, such as an ophthalmic solution. In some embodiments of the present invention, the preparation can further include the use of additional ingredients, such as therapeutic agents, buffers, tonicity adjusting agents, surfactants, viscosity adjusting agents, antioxidants, other agents, combinations thereof, or mixtures thereof.

In yet another aspect, the source of hydrogen peroxide is included in a formulation in an amount sufficient to reduce the concentration of bacteria by at least 3 logs reduction at the fourteenth day after challenge with said bacteria, and to reduce the concentration of bacteria by at least 3 logs reduction at the twenty-eighth day after rechallenge with said bacteria at the fourteenth day. In addition, in further embodiments, the amount of the source of hydrogen peroxide is also sufficient to keep the concentration of yeasts and molds at the fourteenth day after challenge with said yeasts and molds at or below the initial concentration, and to keep the concentration of yeasts and molds at the twenty-eighth day after rechallenge with said yeasts and molds at the fourteenth day at or below the initial concentration.

In a further aspect, the source of hydrogen peroxide is included in a formulation in an amount sufficient to reduce the concentration of bacteria by at least 3 logs reduction at the fourteenth day after an initial challenge with said bacteria, and to reduce the concentration of bacteria by at least 3 logs reduction at the twenty-eighth day after rechallenge with said bacteria at the fourteenth day, wherein the initial challenge is carried out after the formulation has been in storage for 12 months. In one embodiment, the preservative efficacy is demonstrated by the initial challenge that is carried out after the formulation has been in storage for 18 or 24 months.

In still another aspect, a formulation of the present invention is instilled into an affected eye at a dosage of one, two, three, four, or more drops per day, or as prescribed by a skilled medical practitioner. For example, one, two, or three drops of a formulation of the present invention are instilled into an affected eye once, twice, three or more times per day. In certain embodiments, the volume of a drop is about 10-30 µl.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. An ophthalmic formulation consisting of: (a) alginate; (b) a source of hydrogen peroxide selected from the group consisting of urea peroxide and sodium perborate; (c) butylated hydroxyanisole; (d) glycerine; (e) propylene glycol; (f) a borate or phosphate buffer; and (g) optionally EDTA; wherein the source of hydrogen peroxide provides an amount of hydrogen peroxide in the formulation in a range from about 0.001 to about 1 percent by weight of the formulation; and wherein the ophthalmic formulation passes the ISO/DIS 14730 standard preservative efficacy testing with a 14-day rechallenge.

2. The ophthalmic formulation of claim 1, wherein said alginate is present in an amount in a range from about 0.01 to about 10 percent by weight of the formulation.

3. The ophthalmic formulation of claim 1, wherein said alginate is present in an amount in a range from about 0.01 to about 5 percent by weight of the formulation.

4. The ophthalmic formulation of claim 1, wherein said source of hydrogen peroxide provides an amount of hydrogen peroxide in the formulation in a range from greater than 0.01 to about 0.5 percent by weight of the formulation.

5. The ophthalmic formulation of claim 1, wherein said source of hydrogen peroxide provides an amount of hydrogen peroxide in the formulation in a range from greater than 0.1 to about 1 percent by weight of the formulation.

6. The ophthalmic formulation of claim 1, wherein the ophthalmic formulation provides a medicament for treatment for dry eye, allergy of an eye, inflammation of an eye, or infection of an eye.

7. The ophthalmic formulation of claim 1, wherein ophthalmic formulation comprises a solution for treating, cleaning, wetting, or storing contact lenses.

* * * * *